United States Patent
Mueller et al.

(10) Patent No.: US 7,912,549 B2
(45) Date of Patent: Mar. 22, 2011

(54) HOUSING FOR A MEDICAL IMPLANT

(75) Inventors: Niels Mueller, Hamburg (DE); Max Schaldach, Berlin (DE); Wiebke Neumann, Berlin (DE); Werner Uhrlandt, Berlin (DE); Marcel Starke, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 68 days.

(21) Appl. No.: 12/336,659

(22) Filed: Dec. 17, 2008

(65) Prior Publication Data
US 2009/0093855 A1 Apr. 9, 2009

Related U.S. Application Data

(62) Division of application No. 11/567,837, filed on Dec. 7, 2006, now abandoned.

(30) Foreign Application Priority Data

Dec. 8, 2005 (DE) .......................... 10 2005 058 551
Jan. 24, 2006 (DE) .......................... 10 2006 003 224

(51) Int. Cl.
*A61N 1/00* (2006.01)
*H01P 11/00* (2006.01)
*H01S 4/00* (2006.01)
*H05K 3/34* (2006.01)

(52) U.S. Cl. .............. 607/36; 607/37; 607/119; 29/600; 29/592; 29/840; 29/841; 29/842

(58) Field of Classification Search .............. 607/36–37, 607/119; 29/600, 592.1, 840–842
See application file for complete search history.

(56) References Cited

U.S. PATENT DOCUMENTS 3,871,382 A 3/1975 Mann
(Continued)

FOREIGN PATENT DOCUMENTS

DE 3118090 11/1982
(Continued)

OTHER PUBLICATIONS

German Search Report, dated Aug. 16, 2006, 2 pages.
(Continued)

*Primary Examiner* — Niketa I Patel
*Assistant Examiner* — Nicole F Lavert
(74) *Attorney, Agent, or Firm* — ARC IP Law, PC; Joseph J. Mayo

(57) ABSTRACT

Housing for medical implant, such as cardiac pacemaker, defibrillator, cardioverter, etc. Housing including hollow housing and terminal body attached to hollow housing, which has electrical terminal(s), situated in an externally accessible cavity of the terminal body, for connecting an electrode line, and terminal body including a base body made of electrically insulating plastic, connected to hollow housing and carries electrical supply lines and electrical contacts, which are electrically connected thereto, for the electrical terminal so that the contacts are connected via the electrical supply lines to electrical components in the interior of the hollow housing, electrical supply lines being welded to the electrical contacts and the electrical supply lines and electrical contacts, which are welded to one another, being embedded in the base body and thus fixed in their final position, and the base body being glued to the hollow housing using an adhesive between hollow housing and terminal body.

12 Claims, 4 Drawing Sheets

U.S. PATENT DOCUMENTS

| | | | |
|---|---|---|---|
| 5,282,841 | A | 2/1994 | Szyszkowski |
| 5,431,695 | A | 7/1995 | Wiklund et al. |
| 5,851,221 | A | 12/1998 | Rieder et al. |
| 6,080,188 | A | 6/2000 | Rowley et al. |
| 6,205,358 | B1 | 3/2001 | Haeg et al. |
| 6,324,428 | B1 | 11/2001 | Weinberg et al. |
| 6,327,502 | B1 | 12/2001 | Johansson et al. |
| 6,445,948 | B1 | 9/2002 | Somdahl et al. |
| 6,505,072 | B1 | 1/2003 | Linder et al. |
| 6,817,905 | B2 * | 11/2004 | Zart et al. ............ 439/736 |
| 7,187,974 | B2 | 3/2007 | Haeg et al. |
| 2002/0038136 | A1 | 3/2002 | Zaouali et al. |
| 2003/0040780 | A1 * | 2/2003 | Haeg et al. ............ 607/36 |
| 2003/0199941 | A1 | 10/2003 | Nielsen et al. |
| 2004/0068302 | A1 | 4/2004 | Rodgers et al. |
| 2004/0093038 | A1 | 5/2004 | Biggs et al. |
| 2004/0116976 | A1 | 6/2004 | Spadgenske |
| 2004/0215280 | A1 * | 10/2004 | Dublin et al. ............ 607/36 |
| 2005/0033370 | A1 | 2/2005 | Jelen et al. |
| 2005/0131483 | A1 | 6/2005 | Zhao et al. |
| 2005/0203584 | A1 | 9/2005 | Twetan et al. |
| 2007/0270007 | A1 | 11/2007 | Mueller et al. |

FOREIGN PATENT DOCUMENTS

| | | |
|---|---|---|
| DE | 60104241 T2 | 7/2005 |
| EP | 0429024 | 4/1991 |
| EP | 534782 | 3/1993 |
| EP | 0732124 | 9/1996 |
| GB | 2122428 | 1/1984 |
| WO | 96/25978 | 8/1996 |
| WO | 01/99239 | 12/2001 |

OTHER PUBLICATIONS

European Search Report, dated Mar. 5, 2007, 7 pages.

* cited by examiner

HOUSING FOR A MEDICAL IMPLANT

CROSS REFERENCES AND RELATED APPLICATIONS

This application is a divisional of U.S. patent application Ser. No. 11/567,837, filed 7 Dec. 2006 now abandoned and takes priority from German Patent Application DE 10 2005 058 551.5, pending, filed 8 Dec. 2005 and German Patent Application DE 10 2006 003 224.1, pending, filed 24 Jan. 2006, the specification of which are hereby incorporated herein by reference.

BACKGROUND OF THE INVENTION

1. Field of the Invention

The present invention relates to a housing for a medical implant such as an implantable cardiac pacemaker, defibrillator, cardioverter, or the like.

2. Description of the Related Art

A housing for a medical implant comprises a hollow housing, which is used for receiving control electronics, capacitors, and batteries, for example. In addition, the housing comprises a terminal body, which is attached to the hollow housing and has at least one, but typically two to four electrical terminals situated in one or more externally accessible cavities of the terminal body, which are used for connecting one or more electrode lines. Such a terminal body is also referred to as a header. The hollow housing and header together result in a hermetically sealed housing which has the cited electrical components in the interior of the hollow housing, which are connected via supply lines to the electrical terminal or the electrical terminals in the header.

The hollow housing is typically manufactured from biocompatible metal. The electrical connection of the electrical components in the hollow housing to the electrical supply lines located in the header to the electrical terminals typically occurs via bushings which are introduced into a wall of the hollow housing and which terminate the hollow housing with a hermetic seal and, in addition, may also be implemented as filter bushings, which have an electrical low-pass effect.

The terminal housing or the header typically comprises transparent, insulating plastic. The electrical terminals are implemented as sockets, which may receive corresponding plugs of electrode lines. Because of the transparency of the terminal housing, whether an electrode line plug is inserted far enough into the socket of a particular electrical terminal is visible from the outside. The terminal housing may comprise a base body and/or a terminal body, which are connected to one another in a suitable way. Any other construction known from the prior art is also possible, in particular a multipart construction, in which the included components are individually assembled. Therefore, in the following only a terminal housing will be referred to.

High requirements are placed on the quality of a housing for a medical implant. In particular, the hollow housing and terminal housing must work together reliably and tightly over years. The terminal housing itself must be stable and precisely fitted over a long time.

Various approaches are known from the prior art for meeting the above-mentioned requirements. Firstly, casting the terminal housing directly on the hollow housing is known. For this purpose, the hollow housing having supply lines attached thereto for the electrical terminals and contact sockets for the electrode line plugs is inserted into a casting mold and a base body is cast around it by filling the closed casting mold with liquid plastic. The liquid plastic is permitted to cure in the casting mold and results—after removal of the casting mold—in a terminal housing produced in one work step and permanently connected directly to the hollow housing.

Alternatively, pre-mounted terminal housings are known, in which the electrical components, such as electrical contact sockets or electrical supply lines, are first inserted in prefinished injection molded parts made of plastic. Such multipart, pre-mountable terminal housings are known, for example, from WO 01/99239, EP 0 429 024, U.S. Pat. Nos. 5,282,841, or 6,205,358.

BRIEF SUMMARY OF THE INVENTION

The object of the present invention is to provide a housing for an electromedical implant such as a cardiac pacemaker or the like, which allows the simplest possible cost-effective production which is not susceptible to error and results in a housing having the required properties.

This object is achieved according to present invention by a housing of the type cited at the beginning, in which the electrical supply lines are welded to the electrical contacts and the electrical supply lines and electrical contacts which are welded to one another are embedded or extrusion coated in the base body and thus fixed in their final position. The base body is glued to the hollow housing an adhesive between the hollow housing and the terminal body.

In this way, a housing for a cardiac pacemaker results in which the terminal body is prefinished before it is connected to the hollow housing by gluing. This allows the terminal body to be tested in every regard before it is processed further by connection to the hollow housing. It is to be considered that the hollow housing must already have all of the costly electrical components before the hollow housing may be connected to the terminal body (header). Therefore, it is advantageous if the terminal body may be tested in regard to all of its properties before it is connected to the hollow housing by gluing. The mechanical connection between terminal body and hollow housing is simultaneously produced by the adhesive bond between terminal body and hollow housing and, in addition, the required tightness between terminal body and hollow housing is ensured. The adhesive between terminal body and hollow housing thus acts both as a means for transmitting mechanical forces from the terminal body to the hollow housing and as a sealing means.

The electrical lines and electrical contacts are preferably fixed by dual-stage or multistage extrusion coating or embedding.

The base body is at least partially transparent and allows a view of the electrical terminal from outside the terminal body. The base body preferably comprises a transparent plastic which may be processed as cast resin or as a thermoplastic.

The method according to the present invention comprises the following sequential steps: the electrical supply lines, electrical contacts, and the antenna are fixed in an injection mold, in a first injection procedure, the electrical supply lines, the electrical contacts, and the antenna are partially extrusion coated or embedded, subsequently, the molded part is fixed in the injection mold, and then, in a second injection procedure, the electrical supply lines, the electrical contacts, and the antenna are completely extrusion coated or embedded to thus obtain the final form of the terminal body.

In addition, preferably before the fixation of the electrical supply lines, electrical contacts, and the antenna, the supply lines and the contacts may be fixed by a joining technology—especially preferably by welding.

The electrical supply lines, electrical contacts, and the antenna may be fixed by retention means. The retention means are positioned so that the ends of the electrical supply lines and the antenna are fixed. After the retention means are removed, a hollow space which is not extrusion coated thus results, in which an electrical contact having contact pins may then be produced by welding, for example. These contact pins allow electrical contact from the hollow housing. This hollow space may preferably be filled up in a subsequent further injection procedure.

In a further preferred embodiment of the method, one or more of the electrical contacts are pre-mounted using one or more clamping screws, which are used for the screw contact of an electrode line in the plug sockets, and subsequently, in a further injection molding procedure, a cover to seal the screw contact to the outside is injected on or extrusion coated.

A different plastic is preferably used for the second injection procedure than for the first injection procedure. The different requirements for internal fixation and insulation and for external protection of the base body may thus be fulfilled better.

The above-mentioned method may also be implemented advantageously in an injection procedure by welding the supply lines to the electrical contacts, fixing the supply lines and the antenna to one another, and then embedding or extrusion coating them in an injection procedure.

The adhesive with which the terminal body is glued to the hollow housing is preferably epoxide resin or contains epoxide resin. Epoxide resin is distinguished by favorable processing properties and also by favorable properties in regard to the achievable strength and in regard to the biocompatibility. In relation to the achievable strength, it is especially advantageous that epoxide resin both adheres very well to various surfaces, i.e., allows large adhesion forces, and also has good internal tensile strength itself, i.e., develops large cohesion forces.

A light-curing variation of epoxide resin or another adhesive, which cures upon irradiation using electromagnetic radiation in an ultraviolet wavelength range, is especially preferred. UV light-curing adhesives may be processed especially favorably and reliably.

In connection with the use of UV light-curing adhesives, it is advantageous if the base body of the terminal body comprises a material which has a transmission which is sufficiently high in the wavelength range in which the illumination required for curing the adhesive lies to allow curing of the adhesive at a given illumination intensity in at most four times the duration specified for this illumination intensity. In this way, it is ensured that the adhesive cures reliably in a sufficiently short time over the entire area of the adhesive bond between hollow housing and terminal body.

In addition, it is advantageous if the base body is at least partially transparent and allows a view of the electrical terminal or the electrical terminals from outside the terminal body.

A suitable plastic material for a base body made of transparent plastic is polyurethane or epoxide resin. An alternative plastic material for a base body, which is just as suitable, is also polycarbonate or polyurethane.

In addition to those cavities which are used as plug sockets having electrical contacts situated therein, particularly in the form of contact sockets, for receiving a particular terminal plug of an electrode line, the terminal body preferably has at least one further—externally open—cavity, which is used to receive functional assemblies, for example, in the form of an x-ray marker or a cover having at least one sealing stopper. These pre-mounted functional assemblies are inserted or pushed into the corresponding cavities after casting of the base body and, in a special embodiment, are held in position by being fitted (transition or press fitted), a "snap in", or also a "press fit", until they are fixed permanently and tightly in or on the base body by adding adhesive/sealant. A terminal body which is also sealed to the outside in the area of the cavities results in this way.

The cavities for receiving pre-mounted functional assemblies—preferably those of the x-ray marker and the hollow space which results due to the removal of the retention means—are preferably used for a method for gluing the terminal body to the hollow housing before the sealing in that one of the above-mentioned adhesives is applied over these cavities and/or the hollow space and reaches the adhesive gap between the terminal housing and the hollow housing by capillary action.

As already explained, it is advantageous if a particular electrical terminal in the terminal body is formed by at least one plug socket, which is formed by a cavity in the base body and has an electrical contact situated in the plug socket. The electrical contact is preferably a contact socket. The plug socket has a shape which is capable of receiving a terminal plug of an electrode line.

The electrical contacts of the plug sockets are each preferably connected to electrical supply lines, which are formed by flat lines made of conductive and biocompatible material, preferably metal. Known materials for the electrical supply lines are corrosion-retardant steels (e.g., 316 L), cobalt-based alloys (e.g., MP35N), pure titanium (grades 1-4), titanium alloys (grade 5 TiAl6V4), pure niobium, niobium alloys, or other metals known to be biocompatible. The flat lines are preferably each welded to a contact socket of a particular plug socket.

In addition to the electrical supply lines, a further, preferably flat line made of conductive biocompatible material, preferably metal, is preferably provided, which is used as an antenna for a telemetry transmitter and possibly receiver in the interior of the hollow housing. This antenna is embedded together with the supply lines in the base body and thus fixed in its final position. Known materials for the electrical supply lines are corrosion-retardant steels (e.g., 316 L), cobalt-based alloys (e.g., MP35N), pure titanium (grades 1-4), titanium alloys (grade 5 TiAl6V4), pure niobium, niobium alloys, or other metals known to be biocompatible. The flat lines are preferably each welded to a contact socket of a particular plug socket.

The electrical supply lines and the antenna made of flat lines made of conductive material preferably lie in one plane and are preferably produced in bulk. Bulk is understood as single or multiple manufacture of components from a strand-shaped material—for example, strips made of one of the cited materials. The greatest possible minimization of the work steps is thus possible.

To ensure reliable and precisely fitted mounting of the prefinished terminal body on the hollow housing, the base body preferably has two cavities on its side facing toward the hollow housing, which are used for receiving anchors attached to the hollow housing, in the form of pins projecting from the hollow housing, which, together with the cavities, cause precise positioning of the base body, particularly also during the gluing of the terminal body to the hollow housing, and improve the transmission of bending forces between hollow housing and terminal body. The pre-fixing of the base body to anchors may be performed by being fitted (transition or press fitted), by a "press fit" or by "snap in".

In an advantageous embodiment variation, the terminal body has a further cavity for receiving an x-ray marker. This cavity is preferably to be sealed tightly using adhesive, a sealant, or a cover and allows x-ray markers to be inserted for individual identification of a housing after production of the base body.

In regard to shape and volume, the housing is preferably a housing for a cardiac pacemaker, a cardioverter/defibrillator, or a combination of both. In this meaning, a cardiac pacemaker or cardioverter/defibrillator having a housing claimed here is also claimed.

BRIEF DESCRIPTION OF THE DRAWINGS

The present invention will now be explained in greater detail on the basis of an exemplary embodiment with reference to following drawings wherein.

DETAILED DESCRIPTION

Figure 1:
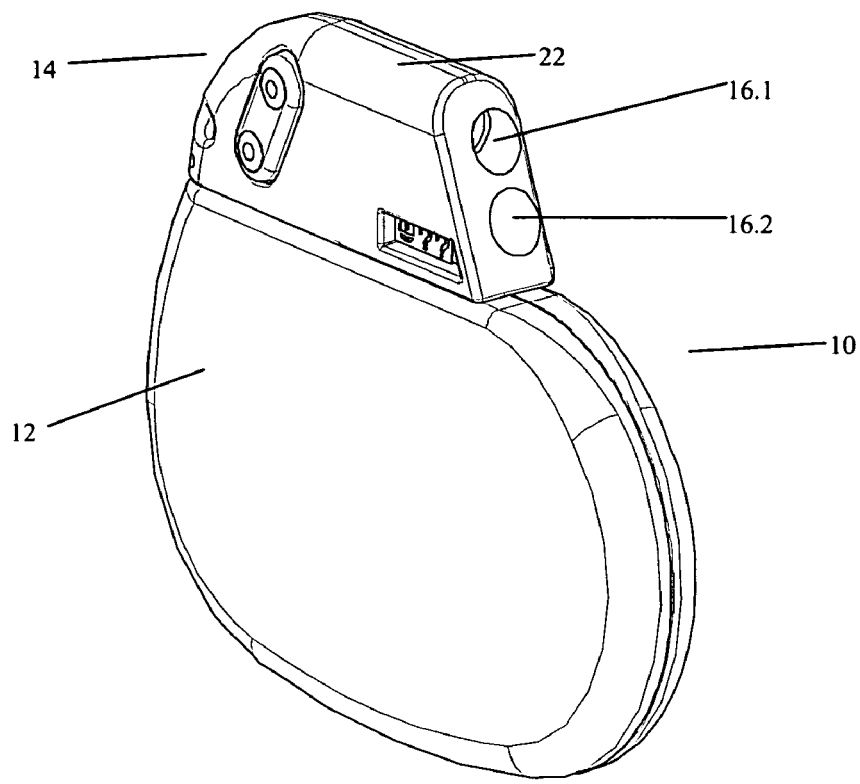
FIG. 1 shows a housing of a cardiac pacemaker having a hollow housing made of biocompatible metal and having a terminal body or header for connecting electrode lines.

FIG. 1 shows a medical implant having a housing 10, which has a hollow housing 12 for receiving batteries, capacitors, and control electronics as well as a terminal body 14—also referred to as a header—which has two plug sockets 16.1 and 16.2, in which plugs of electrode lines are to be plugged.

According to the present invention, the terminal body 14 is glued to the hollow housing 12. For this purpose, an adhesive layer made of epoxide resin, for example, is provided, which is not shown in FIG. 1 and is located between the diametrically opposite faces of the terminal body 14 and the hollow housing 12.

Figure 2:
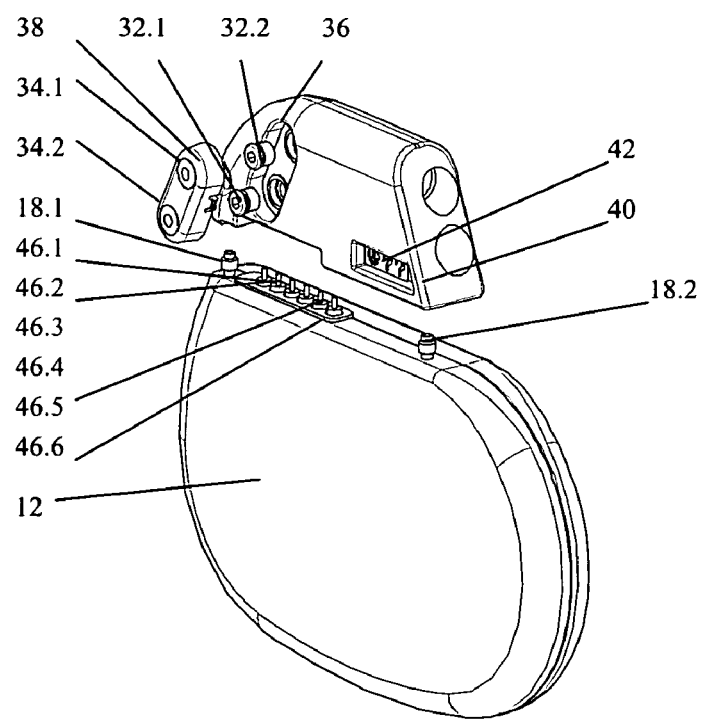
FIG. 2 shows a housing from FIG. 1, illustrated in an exploded drawing having hollow housing and terminal body separated from one another.
Figure 7:
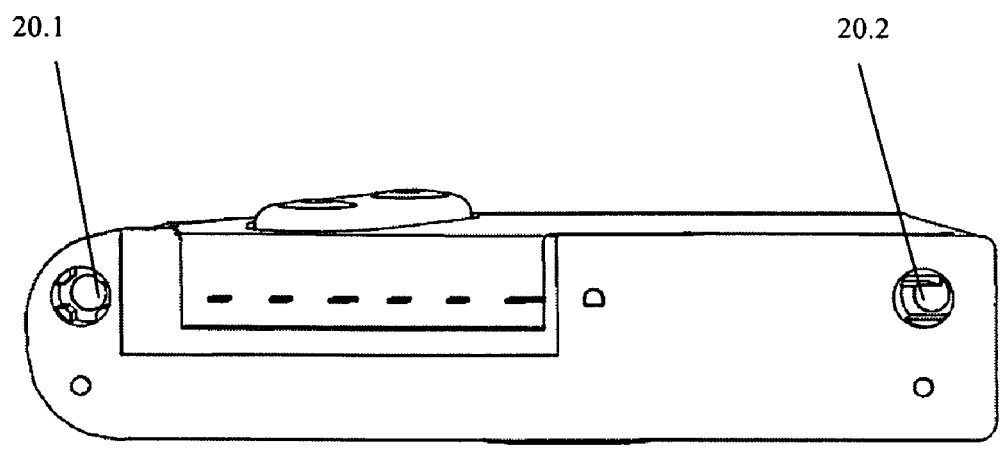
FIG. 7 shows an illustration of the side of the terminal body facing toward the hollow housing.

To make the gluing of terminal body 14 and hollow housing 12 easier—as shown in FIG. 2—two anchors 18.1 and 18.2 are provided on the hollow housing 12, which engage in corresponding cavities of the base body 22 of the terminal housing 14. These cavities 20.1 and 20.2 are shown in FIG. 7. In addition, clamping screws 32.1 and 32.2 in a cavity 36 are shown in FIG. 2, which are closable using a cover 38 and sealing stoppers 34.1 and 34.2 integrated therein. An x-ray marker 42 is situated in a further cavity 40 of the terminal body 14. The hollow housing 12 comprises two hollow housing halves and contains a bushing, using which electrical terminals are guided from the interior of the hollow housing 12 to six electrical contact pins 46.1 through 46.6, which are situated in a row.

Figure 3:
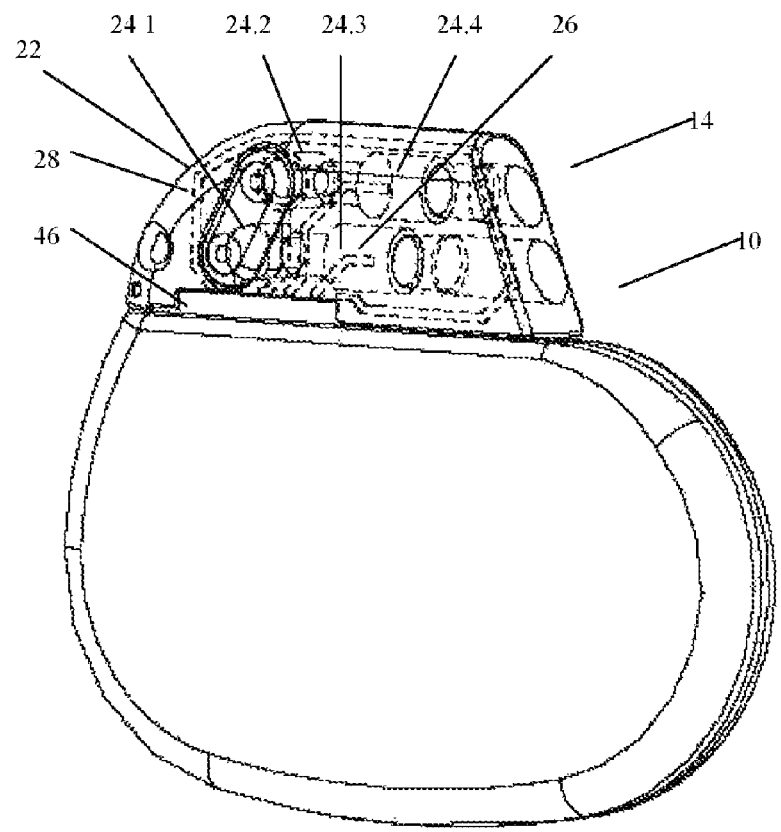
FIG. 3 shows a housing from FIG. 1 having an illustration of the terminal body in a semitransparent mode of illustration.
Figure 4:
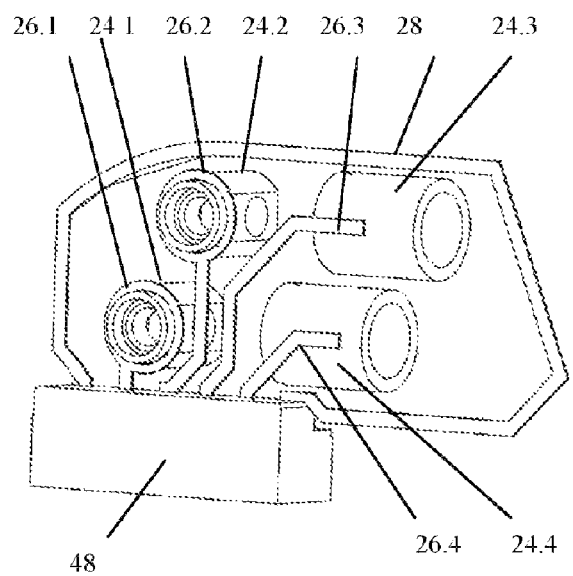
FIG. 4 shows an illustration of electrical supply lines, electrical contacts, and antenna in the pre-mounted state before the casting or extrusion coating and production of the base body.
Figure 5:
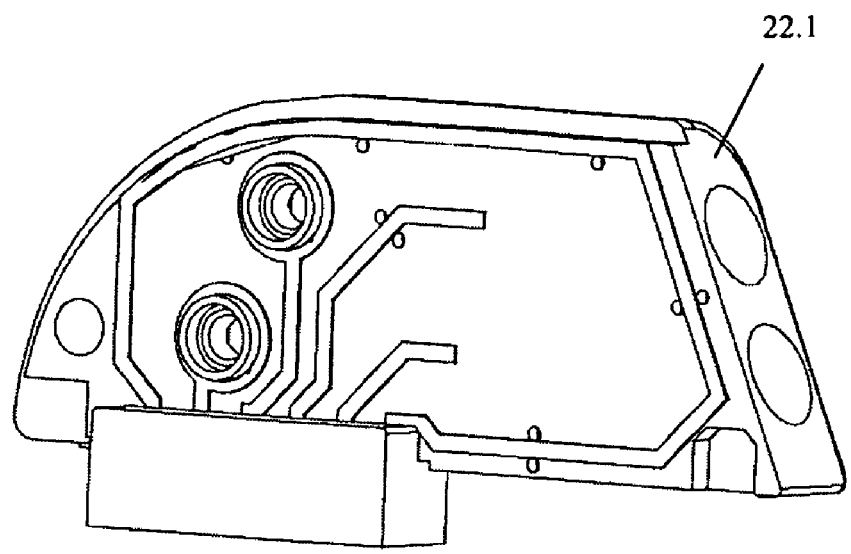
FIG. 5 shows the base body after the first injection procedure.

As may be seen from FIGS. 3 and 4, the terminal body 14 is formed by a transparent base body 22, in which the contact sockets 24.1 through 24.4 and electrical supply lines 26.1 through 26.4 and an antenna 28 are embedded or extrusion coated. The antenna 28 is contacted with the contact pins 46.1 and 46.6 and electrical supply lines 26.1 through 26.4 are contacted with the contact pins 46.2 through 46.4. The electrical supply lines 26.1 through 26.4 lead to the contact sockets 24.1 through 24.4 at the opposite ends.

After the gluing of the terminal body 14 to the hollow housing 12, the contact pins 46.1 through 46.6 are connected to the electrical supply lines 26.1 through 26.4 and the antenna 28 by welding. An initially open cavity 46 is provided for this purpose on the side of the terminal body 14 facing toward the hollow housing 12, which is encapsulated with the supply lines 26.1 through 26.4 and antenna 28 after the welding of the contact pins 46.1 through 46.6.

Figure 6:
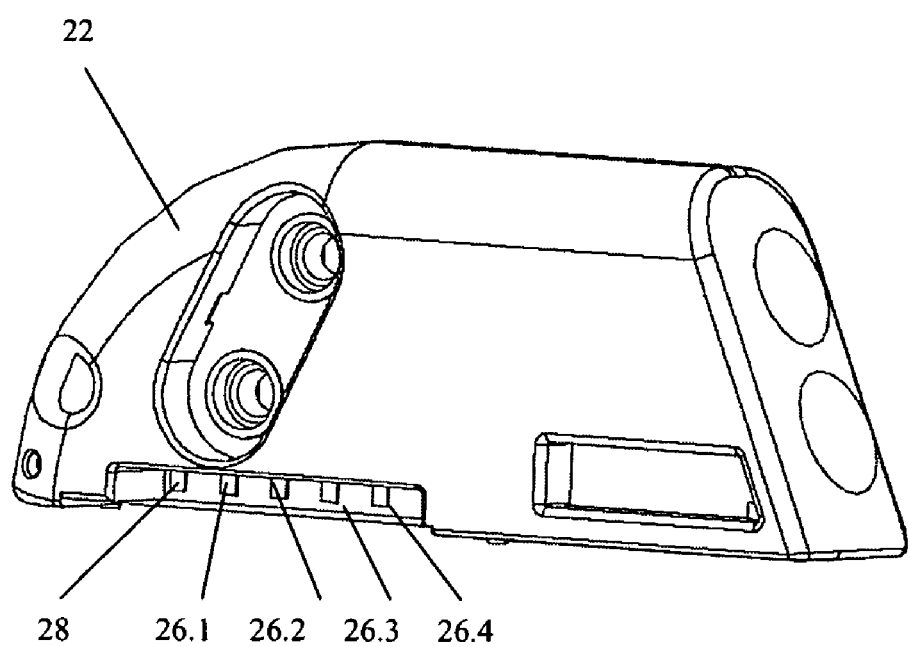
FIG. 6 shows the terminal body after the second injection procedure.

To produce the terminal body 14, firstly the electrical supply lines 26.1 through 26.4 and the antenna 28 are produced, which are connected via a retainer or shared connection 48 to one another. The electrical supply lines 26.1 through 26.4 are welded to the contact sockets 24.1 through 24.4. Subsequently, connection 48 is inserted together with the antenna 28 and the electrical supply lines 26.1 through 26.4 into the casting mold and fixed therein. A first half 22.1 of the base body 22 is initially cast with the aid of this casting mold. This allows the electrical supply lines 26.1 through 26.4 and the antenna 28, which are only a few tenths of a millimeter thick, to be held in position with the aid of pins during the casting. After the first cast half 22.1 of the base body 22 has cured sufficiently, the second half of the base body 22 is cast on the first cast half 22.1, so that the finished base body 22 results, see FIG. 6. The electrical supply lines 26.1 through 26.4, the antenna 28, and the contact sockets 24.1 through 24.4 are permanently embedded in the base body 22. After the base body 22 has been completely produced and cured in this way, the electrical supply lines 26.1 through 26.4 and the antenna 28, which are fixed by the base body 22, may be disconnected from the retainer 48.

Subsequently, the pre-finished terminal body 14 may be placed on the hollow housing 12. The antenna 28 and the electrical supply lines 26.1 and 26.4 are welded to the contact pins 46.1 through 46.6. After mounting of the clamping screws 32.1 and 32.2, the cavity 36 is closed using the cover 38, which contains two sealing stoppers 34.1 and 34.2.

To be able to identify the cardiac pacemaker thus resulting, an individual x-ray marker 42 may finally be inserted in the cavity 40. After the contact pins are welded to the electrical supply lines 26.1 through 26.4 and the antenna 28, the cavity 46 is encapsulated or glued. The connection of the electrode lines to the cardiac pacemaker is produced by inserting corresponding electrode line plugs into the plug sockets 16.1 and 16.2 and fixing the electrode line plugs with the aid of the clamping screws 32.1 and 32.2.

In a subsequent process, the terminal body 14 is glued to the hollow housing 12, the cavities 46 and 40 also being filled with the adhesive. The cover 38 may also be glued to the terminal body in this context.

A suitable material for the base body 22 is transparent polyurethane, which may be cast easily and has the desire mechanical and electrical as well as optical properties, namely, it is transparent. An especially suitable polyurethane is an aliphatic or aromatic acrylic polyester polyurethane.

As already noted, a suitable adhesive for gluing the terminal body 14 to the hollow housing 12 is epoxide resin. A light-during epoxide resin which is activated and cures upon illumination or irradiation with ultraviolet radiation is especially preferred.

What is claimed is:

1. A method for producing a housing for a medical implant having a hollow housing (12) and a terminal body (14) attached therein, which comprises an electrically insulating plastic comprising:
    arranging electrical supply lines and an antenna as flat lines respectively that lie in one plane;
    fixing electrical supply lines,
        electrical contacts, and
        an antenna in an injection mold;
    embedding or partially extrusion coating in a first injection procedure,
        said electrical contacts,
        said electrical supply lines and
        said antenna to form a molded part;
    fixing said molded part in said injection mold; and,
    embedding completely in a second injection procedure,
        said electrical supply lines,
        said electrical contacts and
        said antenna to obtain a final form of a terminal body.

2. The method according to claim 1 further comprising:
    joining said electrical contacts to said electrical supply lines using a weld.

3. The method according to claim 1 further comprising fixing said electrical supply lines, said electrical contacts, and said antenna in said injection mold using a retainer (48).

4. The method according to claim 3 further comprising:
    removing said retainer (48); and,
    filling up hollow spaces resulting when said retainer (48) is removed.

5. The method according to claim 1 further comprising:
    pre-mounting one or more of said electrical contacts using one or more clamping screws; and,
    injecting on or extrusion coating a cover and sealing a screw contact to an outside portion of said cover.

6. The method according to claim 1 further comprising using a different plastic for said second injection procedure than for said first injection procedure.

7. The method according to claim 1 further comprising producing said electrical supply lines and said antenna to lie in a single plane.

8. A method for producing a housing for a medical implant having a hollow housing (12) and a terminal body (14) attached therein, which comprises an electrically insulating plastic comprising:
    arranging electrical supply lines and an antenna as flat lines respectively that lie in one plane;
    joining electrical contacts to said electrical supply lines using a weld;
    fixing said electrical supply lines,
        said electrical contacts, and
        said antenna in an injection mold using a retainer (48);
    embedding or partially extrusion coating in a first injection procedure,
        said electrical contacts,
        said electrical supply lines and
        said antenna to form a molded part;
    fixing said molded part in said injection mold;
    embedding completely in a second injection procedure,
        said electrical supply lines,
        said electrical contacts and
        said antenna to obtain a final form of a terminal body;
    removing said retainer;
    testing said electrical supply lines, said electrical contacts and said antenna of said terminal body before coupling said terminal body to said hollow housing;
    welding said electrical supply lines and said antenna to respective contact pins of said hollow housing;
    gluing said terminal body to said hollow housing; and,
    encapsulating cavity (46) with adhesive.

9. The method according to claim 8 further comprising:
    testing said electrical supply lines, said electrical contacts and said antenna of said molded part before said embedding completely in said second injection procedure.

10. The method according to claim 8 further comprising:
    pre-mounting one or more of said electrical contacts using one or more clamping screws; and,
    injecting on or extrusion coating a cover and sealing a screw contact to an outside portion of said cover.

11. The method according to claim 8 further comprising using a different plastic for said second injection procedure than for said first injection procedure.

12. The method according to claim 8 further comprising producing said electrical supply lines and said antenna to lie in a single plane.

* * * * *